United States Patent
Jackson et al.

(10) Patent No.: US 6,424,859 B2
(45) Date of Patent: *Jul. 23, 2002

(54) DIAGNOSIS OF RHEUMATOID ARTHRITIS IN VIVO USING A NOVEL SPECTROSCOPIC APPROACH

(76) Inventors: Michael Jackson; Michael G. Sowa; James R. Mansfield; Hans H. Eysel; Henry H. Mantsch, all of 435 Elliece Avenue, Winnipeg, Manitoba (CA), R3B 1Y6; Hani El-Gabalawy; Jan M. Canvin, both of c/o University of Manitoba, Department of Medicine, Section of Rheumatology, Rheumatic Disease Unit, 820 Sherbrook Street, Winnipeg, Manitoba (CA), R3A 1R9

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/334,661

(22) Filed: Jun. 17, 1999

(51) Int. Cl.$^7$ .................................................. A61B 6/00
(52) U.S. Cl. .................... 600/475; 250/339.01; 436/63; 436/171
(58) Field of Search ....................... 250/339.12, 339.01, 250/339.06, 341.1; 600/475, 473; 356/301; 436/63, 64, 171

(56) References Cited

U.S. PATENT DOCUMENTS

| | | | |
|---|---|---|---|
| 5,038,039 A | | 8/1991 | Wong et al. |
| 5,197,470 A | * | 3/1993 | Helfer et al. ................ 600/310 |
| 5,473,160 A | | 12/1995 | Eysel et al. |
| 5,699,797 A | * | 12/1997 | Godik ......................... 600/407 |
| 5,807,261 A | * | 9/1998 | Benaron et al. ............. 600/473 |
| 5,876,121 A | * | 3/1999 | Burns et al. ................. 374/161 |
| 5,891,619 A | * | 4/1999 | Zakim et al. .................... 435/4 |
| 5,991,653 A | * | 11/1999 | Richards-Kortum et al. ..... 600/475 |
| 5,999,843 A | * | 12/1999 | Anbar ......................... 600/474 |
| 6,095,982 A | * | 8/2000 | Richards-Kortum et al. ..... 600/476 |
| 6,096,510 A | * | 8/2000 | Hochman .................... 435/29 |

* cited by examiner

Primary Examiner—Brian L. Casler
(74) Attorney, Agent, or Firm—Michael R. Williams; Adrian D. Battison; Ryan W. Dupuis

(57) ABSTRACT

A novel near infrared spectroscopic technique was used to characterize the joints in arthritis with comparison against normal joints. A beam of near infrared light was passed to joints through a fibre optic cable. Scattered light was collected by the same fibre bundle and a spectrum of the joint computed. Multivariate pattern recognition techniques identified regions of the spectrum which allowed discrimination between healthy and affected joints. Linear discriminant analysis resulted in correct classification of 74% of the joints. The high degree of similarity between mean spectra representing the early, late and control groups along with the significant between—subject variability in the data make diagnosis based on visual assessment of the spectra impossible. Linear discriminant analysis was therefore applied to spectra to determine if spectra could be classified by statistical methods as arising from early or late RA. Application of LDA resulted in correct classification of 74% of the joints. Interestingly, the spectral regions in which diagnostic differences were found by the multivariate analysis contain absorption bands related to tissue oxygenation status (oxy and deoxyhaemoglobin) and oxygen utilisation (cytochrome aa$_3$), suggesting that ischaemic changes within the joint are being detected.

14 Claims, 2 Drawing Sheets

DIAGNOSIS OF RHEUMATOID ARTHRITIS IN VIVO USING A NOVEL SPECTROSCOPIC APPROACH

FIELD OF THE INVENTION

The present invention relates generally to the fields of diagnostic devices and methods of use thereof. More specifically, the present invention relates to a device for diagnosing rheumatoid arthritis.

BACKGROUND OF THE INVENTION

There are almost 100 disorders that fall under the umbrella classification of arthritis. The most prevalent are osteoarthritis and rheumatoid arthritis. Osteoarthritis (OA) is a disease of wear and tear commonly affecting the elderly. Rheumatoid arthritis (RA) is a systemic auto-immune disorder causing a symmetric inflammatory polyarthritis. Once the inflammatory process is activated, there can be rapid destruction of joints that can, in some cases, be very aggressive. It has been shown that erosive damage occurs within weeks of the onset of the clinical symptoms. Typically, RA involves the small joints of the hands and feet leading to the clinical signs of joint tenderness and swelling.

Despite its prevalence, arthritis can often be a difficult disease to diagnose. Clinical history and physical examination by a specialised medical practitioner are of key importance in diagnosis. However, any diagnosis based upon the personal skills and experience of the examining physician must of necessity contain an element of subjectivity. Among the more objective tests are X-ray investigation and magnetic resonance imaging of the affected joints and serological and immunological analysis of synovial fluid and blood.

Once a diagnosis is made, assessment of prognostic indicators presents further difficulties. For example, RA has traditionally been thought of as one homogeneous disease, but it has become increasingly obvious that there are many subgroups within the patient population. Specifically, while some patients may have minimal disease for 20–30 years with only minor joint deformities and mild disability, other patients may have the disease for less than 5 years and within this time the disease progresses so rapidly that many joints are destroyed and require replacement. Patients in this latter group often have severe functional disabilities in their activities of daily living.

It is becoming clear that there are certain early prognostic features that can suggest that a patient is more likely to have extensive and progressive disease, at least for RA. One of these features is the immunological haplotype where the class 11 MHC HLA-DR 4 and HLA-DR 1 are associated with RA. Unfortunately, immunogenetic haplotyping is expensive and is not a practical tool for the office. Other factors contributing to a poorer prognosis include female gender, high rheumatoid factor titres, multiple joint involvement and early erosive damage. However, no one feature predicts the severity of disease or the extent of involvement at a specific joint.

Current modes of assessment of arthritis (other than clinical examination) include i) plain radiographs, which do not show the very early damage: ii) magnetic resonance imaging which does show early cartilage and bony destruction, but is neither easily available nor inexpensive; and iii) ultrasound imaging which provides a more subjective assessment but thus far has been confined to research units.

All of the above diagnostic methods, and particularly combinations of these methods, may require the services of a rheumatology specialist, immunologist and skilled technical staff, making diagnosis costly, labour intensive and time consuming. In addition, it may take weeks or months for the clinical symptoms to become distinctive enough to allow diagnosis. Unfortunately, by the time symptoms are sufficiently distinct to allow diagnosis by more objective methods, considerable irreversible damage may already be present in the affected joints.

Clearly, it is critical to determine the severity of the disease early on in the clinical assessment. However, this is complicated by the discordance that is often found between the detection of swelling, tenderness and temperature of a joint with plain radiographic assessment which may not yet show any underlying damage. Although the majority of patients with active synovitis do progress on to early radiographic damage, there is a subset of patients who have active synovitis for several years with no apparent radiographic joint damage.

New methods for the early investigation of arthritis are therefore required and infrared spectroscopy may form the basis for such a method. For example, U.S. Pat. No. 5,038,039 teaches an infrared spectroscopy-based method for detecting the presence of anomalies in biological tissues and cells. However, the tissues and/or cells must be removed from the patient in order to be tested.

Similarly, U.S. Pat. No. 5,473,160 teaches a method for diagnosing arthritic disorders using infrared spectroscopy that involves analyzing synovial fluid taken from a joint for anomalies.

It is apparent that there is a real need for a rapid, non-subjective method for the diagnosis of arthritic disorders that has the additional benefits of being low cost, non-labour intensive and does not require the removal of fluid or tissue samples from the patient, that is, a method of diagnosing arthritis that is non-invasive.

SUMMARY OF THE INVENTION

The novel method presented here is based upon the combination of near infrared (NIR) spectroscopy with multivariate classification.

NIR spectroscopy measures the wavelengths of near infrared light that are absorbed by a sample, which produces a characteristic fingerprint of the sample. NIR light is absorbed to promote vibrations within molecules. Typically, only absorption band from O—H, N—H and C—H vibrations are seen. The wavelengths of light which are absorbed depend upon the nature of the vibration (stretching, bending etc.) and the nature of the molecules in the bond. Thus, O—H stretching and N—H bending vibrations absorb different wavelengths of light. In addition, NIR light can be absorbed to promote low-lying electronic transitions in the metal ions found in proteins such as haemoglobin, myoglobin and cytochromes. The wavelength of light absorbed by the metal ions is influenced by both the oxidation state and local environment. Thus, oxy- and deoxymyoglobin, oxy- and deoxyhaemoglobin and reduced and oxidised cytochrome $aa_3$ all absorb different wavelengths of near infrared light.

It can be seen that the wavelengths of near infrared light absorbed by tissues will provide direct chemical (compositional) and physiological (oxygenation and oxygen utilisation) information. More importantly, near infrared spectroscopy is sensitive to changes in these parameters. In principle, this should allow NIR spectroscopy to be used as a tool to assess joint physiology. We have therefore applied NIR spectroscopy to the characterisation of rheumatoid synovitis.

According to a first aspect of the invention, there is provided a method of diagnosing an inflammatory or ischaemic condition in a joint comprising:

providing a device having:
an emitter arranged to emit a beam of infrared light;
a collector arranged to collect and analyze reflected light, said collector for producing an infrared spectrum; and
a database containing a plurality of spectra previously collected from joints, said spectra being divided into at least two groups: spectra from joints diagnosed as having the inflammatory or ischaemic condition and spectra from nonafflicted joints;
providing a joint;
positioning the device proximal to the joint such that the emitter contacts the joint;
emitting a beam of near infrared light from the emitter into the joint;
collecting and analyzing reflected light from the beam, thereby producing a patient spectrum;
comparing the patient spectrum to the database spectra; and
assigning the patient spectra to a group, thereby diagnosing the joint.

The inflammatory or ischaemic condition may be rheumatoid arthritis.

The patient spectrum may be a mean spectrum of two or more spectra of the joint.

The patient spectrum may be compared to the database spectra over wavelengths of high accuracy.

The wavelengths of high accuracy may be selected from the group consisting of: wavelengths corresponding to oxyhemoglobin to deoxyhemoglobin ratio; wavelengths corresponding to reduced cytochrome $aa_3$; wavelengths corresponding to oxidized cytochrome $aa_3$; wavelengths corresponding to deoxyhemoglobin; wavelengths corresponding to oxyhemoglobin; wavelengths corresponding to cytochrome $aa_3$; wavelengths corresponding to water; wavelengths corresponding to proteins; wavelengths corresponding to lipids; and combinations thereof.

The emitter may be a fibre optic probe.

The database spectra may be divided into three groups: control, early rheumatoid arthritis and late rheumatoid arthritis.

According to a second aspect of the invention, there is provided a device for diagnosing an inflammatory or ischaemic condition in a joint comprising:

an emitter arranged to emit a beam of infrared light;
a collector for producing an infrared spectrum from reflected infrared light; and
a database containing a plurality of prior spectra previously collected from joints, said spectra being divided into at least two groups: spectra from joints diagnosed as having the inflammatory or ischaemic condition and spectra from nonafflicted joints; and
an analyzer for comparing the spectrum to the prior spectra and assigning the spectrum to a group, thereby diagnosing the joint.

The inflammatory or ischaemic condition may be rheumatoid arthritis.

The collector may produce a spectrum that is a mean spectrum comprised of two or more spectra of the joint.

The analyzer may analyze the spectrum for wavelengths of high accuracy and compares the spectrum to the database spectra over the wavelengths of high accuracy.

The emitter may be a fibre optic probe.

The spectra may be divided into three groups: control, early rheumatoid arthritis and late rheumatoid arthritis.

Figure 1:
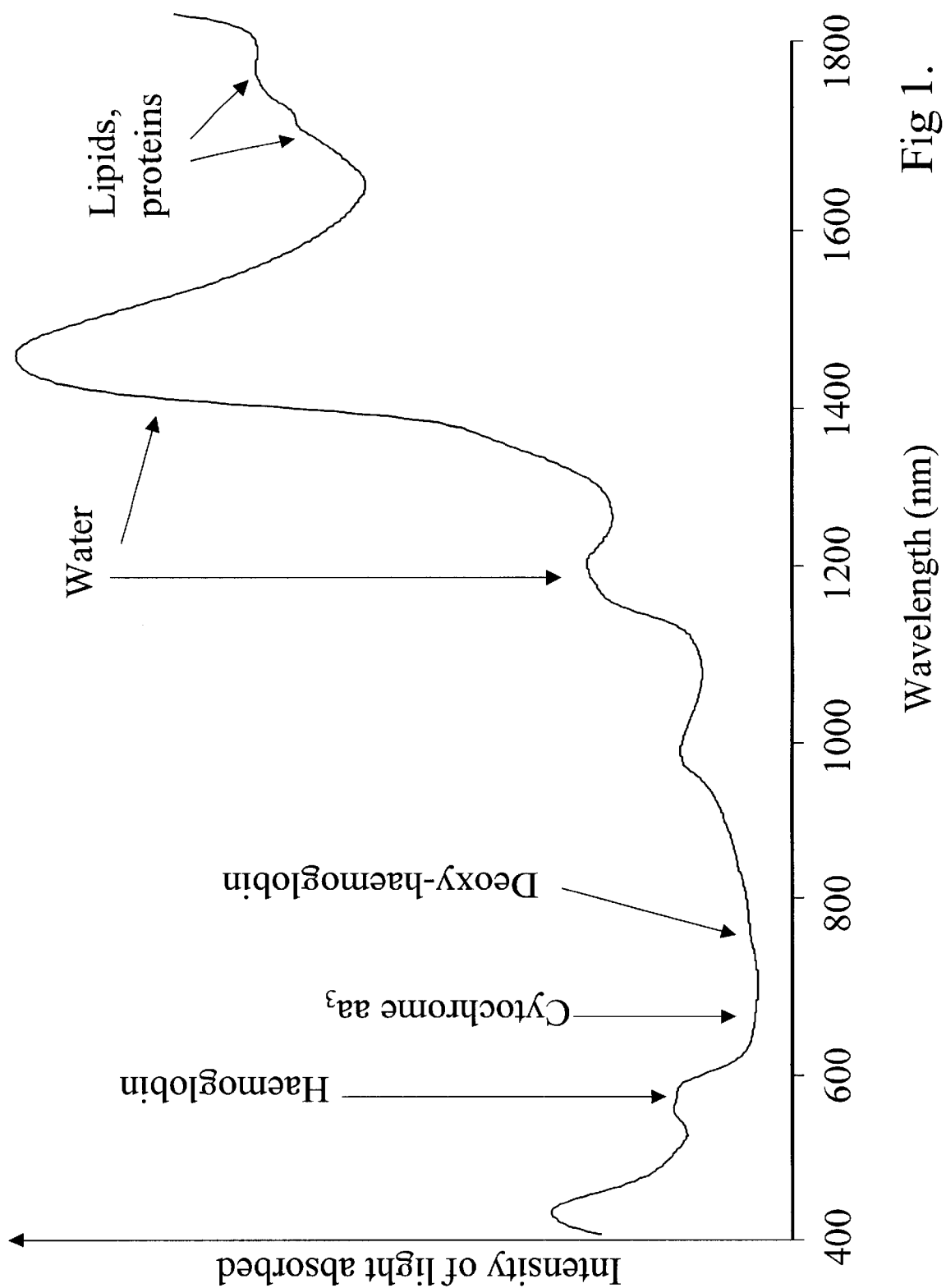
FIG. 1 is a representative spectrum of a PIP joint.

TABLE 1 is a summary of baseline characteristics of patients.

TABLE 2 is a summary of total joint count, radiographic damage and laboratory parameters.

TABLE 3 summarizes two class LDA of early RA and late RA, PIP only.

TABLE 4 summarizes two class LDA of early RA and late RA, MCP only.

TABLE 5 summarizes two class LDA of early RA and late RA, both MCP and PIP.

TABLE 6 summarizes three class LDA of control, early RA and late RA (all joints).

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, "oedema" refers to an abnormal accumulation of fluid in body parts or tissues.

As used herein, "synovial fluid" refers to the fluid secreted by the synovial membrane that lubricates joint surfaces and nourishes articular cartilages.

As used herein, "inflammation" refers to the physiological response of the body to tissue injury.

As used herein, "ischemic" refers to a local decrease in blood supply.

Described herein is a device for assessing the condition of a joint suspected of being arthritic. The device comprises an emitter arranged to emit a beam of low intensity near infrared radiation, a collector which records the absorbance of NIR light at different wavelengths and a database containing spectra from joints previously determined clinically to be normal or arthritic. As discussed above, biomolecules absorb NIR radiation at characteristic wavelengths. Thus, the described device can be used to take a chemical and physiological fingerprint of a joint and then compare the resulting spectrum to a set of spectra in the database for classifying the joint. In one embodiment, the device is positioned such that the emitter is in contact with a joint. The infrared beam is then emitted and collected, producing a spectrum. In one embodiment, this process is repeated twice more and the spectra are averaged by an automated computer algorithm, producing a mean spectrum. The mean spectrum is then analyzed by another computer algorithm for regions of high diagnostic utility. The mean spectrum is then compared to the spectra in the database over these regions by a computer algorithm. On the basis of this comparison, the mean spectrum is assigned to a specific group of spectra (early arthritic, late arthritic or control). Thus, the condition of the joint can be assessed at an early stage without the need to remove a fluid or tissue sample. Furthermore, because assessment can be done at an early stage, treatment can begin before excessive and irreversible damage to the joint has occurred. Furthermore, the spectra from the examined joint can be added to the database, meaning that the accuracy of the device continually improves as more data is gathered.

We have recently shown that analysis of synovial fluid by infrared spectroscopy can be used to predict the involvement of joints in a range of arthritic disorders. We have now taken this approach one stage further, and applied near infrared spectroscopy (NIRS) to the differentiation of arthritic and control joints and to see if NIRS could determine early and late involvement in rheumatoid arthritis.

Near infrared spectroscopy potentially provides a sensitive means of monitoring tissue by directly measuring the chemical composition of tissues. Materials such as lipids, proteins, water, oxyhaemoglobin, deoxyhaemoglobin and reduced and oxidised cytochrome $aa_3$ each absorb characteristic wavelengths of infrared light. By analysing the relative proportions of light absorbed at each of these wavelengths, a chemical fingerprint of tissue can be obtained. In the case of the small joints of the hand, a beam of low intensity near infrared light is directed onto the joints via a fibre optic bundle. The light which is reflected back from the joint is collected and analysed to determine which wavelengths of light have been absorbed, A plot of the intensity of light absorbed as a function of wavelength produces a chemical fingerprint of the joint. Specifically, oxyhaemoglobin and deoxyhaemoglobin indicate oxygen delivery to the synovium and surrounding tissue while the redox balance of cytochrome aa3 provides a measure of mitochondrial oxygen utilisation. In addition, tissue oedema associated with inflammation can be detected pre-clinically using near infrared spectroscopy. That is, high levels of water can be detected by the above-described device. This in turn means that near infrared spectroscopy can be used to detect inflammatory and ischaemic conditions in the joint.

The invention will now be described by way of examples; however, the invention is not limited to the examples.

EXAMPLE I

Patient Selection

A cohort of 53 patients with rheumatoid arthritis (meeting ARA criteria) were studied. Of these, 28 had RA of duration less than 2 years (early RA) and 25 had RA of duration greater than 2 years (late RA). The control groups consisted of 8 age and gender matched subjects with no RA. Demographic information was obtained on the patient's age, gender, ethnicity, smoking history and hand dominance. All patients were between 18 and 70 years of age. Clinical evaluation for joint swelling and tenderness, on a graded scale, was performed on the second and third metacarpal phalangeal (MCP) and proximal interphalangeal (PIP) joints bilaterally. Patients were excluded if there were superimposed changes of osteoarthritis on clinical or radiographic assessment. A graded total joint count on 28 joints was performed for swelling, tenderness and damaged joints. Self-evaluation of morning stiffness, pain by visual analogue scale and functional disability with a modified Health Assessment Questionnaire (HAQ) was performed. Laboratory parameters for erythrocyte sedimentation rate (ESR) and C-reactive protein (CRP) were determined. Radiographs of the hands were taken and scored at the 8 target joints by a panel of 3 rheumatologists, blinded to the results. Using this information, patients were classified as control, early RA or late RA.

The baseline characteristics, total joint counts, radiographic damage score and laboratory parameters are summarized in Tables 1 and 2. As can be seen, significant differences existed between the mean disease duration, swelling, damage and radiographic scores between early and late RA, with values being higher in the late RA group as expected.

EXAMPLE II

Near Infrared Spectroscopy

Visible and near-IR spectra were acquired using a Perstorp NIRSystems model 6500 scanning spectrometer (Silver Springs, Md.) equipped with a randomized fiber bundle with an active area of approximately 1 cm. Triplicate spectra were collected in the wavelength range of 400 to 2500 nm at 2 nm resolution by co-averaging 64 scans. In this embodiment, 64 scans were performed to increase the signal to noise of the data. That is, all spectra contain random noise; by averaging a number of scans which each contain random noise, the random noise is cancelled out. As will be apparent to one knowledgeable in the art, the more scans that are averaged, the more random noise that is cancelled out. In this spectra region, it is found that 64 scans is a good compromise between the time required to make multiple scans and the quality of the data. However, it is apparent that other arrangements, wherein either a greater number or lesser number of scans are taken, may also be suitable, depending upon experimental conditions. As will be apparent to one knowledgeable in the art, most NIR instruments include a feature that allows the number of scans to be averaged to be selected. Spectra were acquired by bringing the near infrared light from the spectrometer to the joints using a fibre optic probe. The fibre optic probe was pressed very lightly against the joint and the reflected light collected. Through analysis of the reflected light the wavelengths of light absorbed by each joint were calculated. Thus, the spectra were gathered without the removal of a sample of any kind from the patient.

Prior to any further analysis, the triplicate spectra from each joint were averaged, taking the median value for each wavelength, and then the spectral width was truncated to 400 to 1860 nm, leaving a total of 731 data points per spectrum. The spectra were partitioned into 3 classes: control, early RA and late RA and a mean spectrum and the standard deviation for each data point was calculated for each class. Any spectrum which had at least one data point whose value was more than three standard deviations from the class mean was removed as an outlier. This left 94 control spectra, 205 early RA spectra, and 193 late RA spectra, for a total of 492 spectra.

EXAMPLE III

Multivariate Analysis

To increase accuracy and decrease processing time, spectra were first pre-processed. The pre-processing method used here selects relevant features from the spectra by an optimal region selection (ORS) algorithm developed in-house. ORS starts at one end of an N-point spectrum by selecting a window consisting of $M \ll N$ adjacent data points. Typically, $M=10-12$. Linear discriminant analysis (see below) is carried out with these M points as local attributes, and the classification accuracy on the test subsets is recorded. The window is advanced by M/2 data points along the spectrum and the process repeated. When the spectra are fully traversed, the non-overlapping subregions are sorted in decreasing order of accuracy. If the best subregion found satisfies a prescribed accuracy (typically $\geq 90\%$), the subregion selection process is terminated. This happens rarely, and thus the next stage is initiated. The best 6–8 subregions are tested in all possible combinations and the least number L of subregions that satisfies the accuracy criterion provides spectral regions that are used for classification.

Classification of spectra was performed by linear discriminant analysis of the optimal set of spectral subregions. A linear discriminant analysis algorithm was trained to recognise the patterns in these subregions which were characteristic of early and late RA and control joints. Two thirds of all of the spectra were used in this training step. The remaining spectra were used as a test set, to see if the LDA algorithm could correctly predict whether the pattern corresponding to early RA, late RA or control joints was present.

EXAMPLE IV

Results And Discussion

A representative spectrum of a PIP joint is shown in FIG. 1. Spectra are plotted showing the amount of light absorbed by the joints at each wavelength. Thus, peaks correspond to wavelengths of light which are absorbed by materials within the joint. The more intense the peak, the more light is absorbed by the joint and the higher the concentration of material that is absorbing the light within the joint. Since, as discussed above, biomolecules absorb characteristic wavelengths of light, each peak in the spectrum can be assigned to specific substances found in the joint. By comparison with spectra of reference materials, we can assign the major peaks as shown in FIG. 1. The major absorption bands arise from water (in synovial fluid, blood, interstitial fluid and within cells). Other important, but weaker, absoprtions arise from oxy-haemoglobin, deoxy-haemoglobin, cytochrome $aa_3$ and lipds and proteins. This is important, as oxyhaemoglobin and deoxyhaemoglobin indicate oxygen delivery to the synovium and surrounding tissue while the redox balance cytochrome $aa_3$ provides a measure of mitochondrial oxygen utilisation.

Traditional univariate statistical tests can be applied to spectra, if one considers a spectrum to be simply a plot of magnitudes at each point in the spectrum. We can then calculate the mean intensity and variance of light absorbed at each wavelength for the three classes and the results can be analysed by Student's t-test or analysis of variance. However, application of such univariate statistical tests reveals that no significant differences in the amount of light measured are seen between groups at most wavelengths, most likely due to the high degree of variability between spectra from different subjects.

Figure 2:
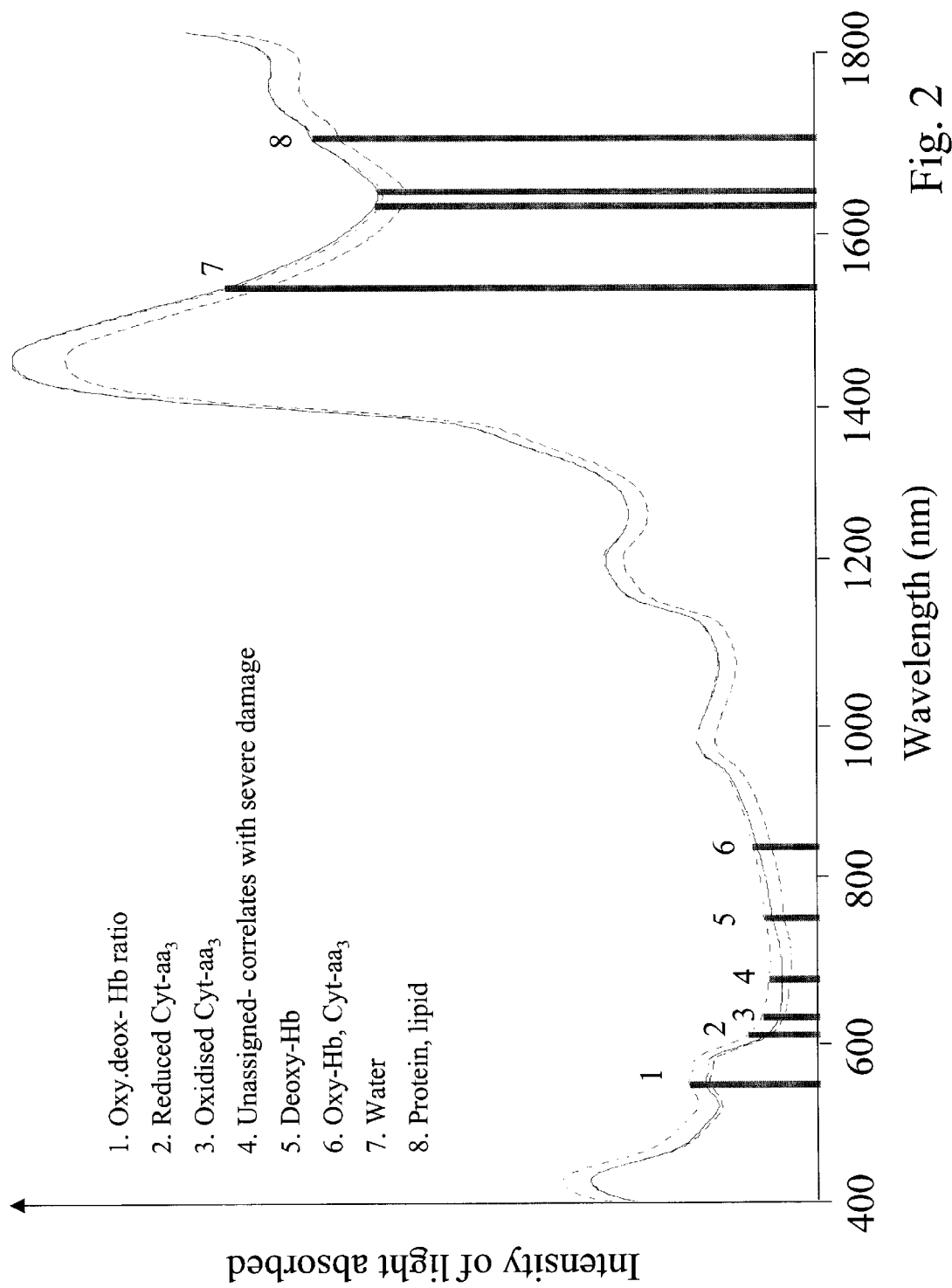
FIG. 2 is mean spectra of control, early and late RA joints.

Class average (mean) spectra of all early RA, late RA and control joints are shown in FIG. 2. It is immediately apparent that the mean spectra show a high degree of similarity, and discrimination between spectra of early RA, late RA and control joints is difficult, even for the trained spectroscopist.

It is highly improbable that variations in the absorption of a single wavelength of light will provide information which is clinically useful: this would imply that a single chemical species can be used as a diagnostic marker for RA. For disease as complex as RA, this seems unlikely. If this was indeed the case, then it seems likely that a diagnostic tests based upon this chemical species would have been developed. However, tests based upon a single clinical or laboratory parameter are rarely diagnostic for RA. In general, more than one parameter (variable) is required to diagnose and stage the disease. Thus, the current clinical evaluation of RA is a multivariate process.

In a similar fashion, it may be expected that multivariate analysis is required to obtain diagnostic information from NIR spectra of joints. A visible—near infrared spectrum of the joint is intrinsically multivariate since the tissue reflectance properties are measured over a series of wavelengths. Thus, rather than analysing the response at a single wavelength of the spectrum, parameters can be derived from the response across a range of wavelengths. For instance, tissue water content can be derived by integrating the response across all regions of the spectrum where water absorptions dominate, rather than a single wavelength. Another commonly measured near infrared spectral parameter is tissue hemoglobin oxygen saturation, which requires analysis of a number of absorption peaks. A number of multivariate statistical methods are available which can assess tissue responses across the spectrum and correlate these responses with clinical data.

To reliably ascertain whether or not significant differences exists between the three classes of spectra that are of diagnostic use, multivariate pattern recognition methods are required. Utilizing the reflectance response over several spectral regions or over the full spectral range improves the power of the multivariate statistical tests in the presence of confounding variables.

Principal component analysis (PCA) is a powerful multivariate technique for assessing spectra. PCA partitions the variance of the spectroscopic data set into its independent sources and rank orders these sources of variation. In other words, the first principal component (PC) of the spectral data set consists of the linear combination of variables (wavelength responses) which account for the greatest variation within the population. The second PC accounts for the next largest source of variation with the restriction that it is unrelated or independent (orthogonal) to the first component. Higher PCs account for successively less variation within the data set subject to the same independence constraint. The variance partitioning carried out in a principal component analysis is solely based on the intrinsic covariance structure of the data set and does not consider any of the clinical or radiographic scores. As such, it is generally referred to as a model-free or exploratory method of data analysis.

Once the PCs have been determined it is then possible to establish a correlation for each PC with clinical data. Correlating the intrinsic variance structure of the spectroscopic data set with the clinical and radiographic data reveals some interesting relationships. For instance, the joint damage score shows a small but statistically significant correlation with the $1^{st}$ PC of the spectroscopic data. The clinical tenderness score is significantly correlated with both the $2^{nd}$ and $3^{rd}$ PCs of the spectroscopic data. Tenderness was also found to correlate significantly with tissue water content and oxygenation as measured by near infrared spectroscopy. The joint swelling score was found to have a significant correlation with the $4^{th}$ PC of the spectroscopic data as well as hydration and oxygenation. Since swelling and tenderness are often associated with inflammation, a correlation with tissue oxygenation and water content may be expected. However, the correlation between PCs and the clinical/ radiographic scores suggest that further biochemical manifestations leading to the observed clinical symptoms of tenderness and swelling as well as hard tissue damage are latent in the visible-near infrared spectra. In fact, manifestations of joint damage appear in the PC describing the greatest variation in the spectroscopic data over the study population. This may suggest that joint damage causes the greatest change in the spectral response of the joint. Tenderness appears to be correlated with less drastic variations in the spectra which emerge only in the $2^{nd}$ and $3^{rd}$ PC, while swelling seems to give rise to even more subtle spectroscopic changes which appear in the $4^{th}$ PC.

PCA clearly demonstrates that spectral information can be correlated with some clinical features of arthritis. However, while principal component analysis finds the linear combination of wavelengths (variables) which maximize independent sources of variation within the data set, it does so with no regard to the clinical grouping of the patients. Sources of variation which are not related to disease state are also accounted for in a PCA. A more reliable model can be developed using the combination of wavelengths (variables) which optimally discriminate between the clinical groups. This amounts to searching all of the variables present in the data set for patterns characteristic of the disease state. In other words, a pattern recongition model can recognise a spectroscopic fingerprint characteristic of a particular type (or stage) of disease.

Multivariate pattern recognition techniques such as cluster analysis, linear discriminant analysis (LDA) and neural network analysis are being increasingly applied to complex spectroscopic data to allow classification of tissue into clinically relevant groups. The simplest multivariate pattern recognition techniques are the unsupervised methods, of which cluster analysis is the most popular. Cluster analysis techniques compare spectra in a data set and calculate some measure of similarity between spectra. Spectra are then grouped based upon the degree of similarity, with spectra having a high degree of similarity being placed in the same group or cluster. An important shortcoming of these unsupervised clustering techniques is the sensitivity of the methods to noise and outliers. More sophisticated, supervised pattern recognition methods such as linear discriminant analysis (LDA) make use of the fact that we are often in possession of the class identity for each spectrum, i.e. we know the diagnosis. Spectra can then be assigned into classes, depending upon the diagnosis. In this case we have three classes, early RA, late RA and control. The LDA algorithm then analyses the spectra in each class, searching for the pattern within the spectrum which is characteristic of that class. For example, the LDA algorithm attempts to find a combination of absorbance intensities at a variety of wavelengths that are only seen when a joint is affected by early RA. It then attempts to find a combination of absorbance intensities at a variety of wavelengths that are only seen in late RA. In this way any new spectrum from an undiagnosed patient can then be analysed to see which of these characteristic patterns is present. Such methods are more suited to the difficult task of classifying spectra based upon very subtle differences in the presence of outliers and noise.

Linear discriminant analysis combined with a genetic algorithm (Optimal Region Selection, or ORS) was the multivariate pattern recognition technique applied to our data, chosen for speed and robustness. Data was split into a training set (used by the LDA algorithm to find the pattern characteristic of each of the three classes) and a test set used to evaluate the accuracy of the trained algorithm. To reduce processing time, ORS divided the spectrum into a number of smaller regions. Linear discriminant analysis was then applied to every combination of these subregions, to determine which combination of n sub-regions (where n is typically much smaller than the total number of sub-regions) provides the most accurate discrimination between spectra in the three classes. The spectra were then divided into an entirely different set of sub-regions and the process was repeated. This process was repeated through 250 iterations and the combination of subregions providing the most accurate classification of spectra into the three groups was determined. Spectra in the test set were then divided into these sub-regions and LDA performed. The classification of spectra from each patient in the test set was then compared to the clinical diagnosis. This analysis was applied to spectra from PIP and MCP joints separately and also to pooled spectra of PIP and MCP joints.

We applied the multivariate classification strategy described in the material and methods section to our data. Application of the Optimal Region Selection subroutine results in the identification of a number of subregions (highlighted in FIG. 2) which allowed optimal classification. Classification was then performed using only these spectral subregions. For each problem, the LDA was trained using two thirds of the spectra in the data base and the trained algorithm then applied to the remaining spectra.

The result of LDA applied to all PIP spectra to distinguish between early and late RA is shown in Table 3. When the trained algorithm is then applied to the test spectra, 70.3 and 52.9% of early and late RA joints respectively could be correctly predicted (overall accuracy 61.6%). Specificity, positive predictive value and negative predictive values are within the same range.

The result of LDA applied to all MCP spectra to distinguish between early and late RA is shown in Table 4. The sensitivity of the method for MCPs is much improved compared to that seen for PIP spectra, with 78.8 and 72.7% of joints being correctly classified as early and late RA respectively, with an overall accuracy of 75.8%. Specificity, positive predictive value and negative predictive value are also substantially improved, all values being greater than 70%.

These results suggest that the method is more sensitive to the presence of RA in MCP points than PIP joints. In total, using two classification strategies (i.e one for MCP and one for PIP joints) 69% of joints were correctly classified as either early or late RA. Interestingly, combining the spectra for MCP and PIP joints results in better overall performance of the linear discriminant analysis (Table 5). Applying LDA to the combined data set resulted in correct classification of joints as either early or late RA with an accuracy of 77.3 and 71.2% respectively (overall accuracy 74.3%), with specificity and positive and negative predictive values all being greater than 70%.

Finally, LDA was used to discriminant between early RA, late RA and control joints (Table 6). As combining data from MCP and PIP joints was found to improve classification for the two class problems discussed above this approach was used for the three class problem. Joints could be predicted as early RA, late RA or control with an accuracy of 77.7, 74.6 and 69.9% respectively (overall accuracy 74.1%). Specificity and positive and negative predictive values are also high.

The optimal subregions used in the linear discriminant analysis are highlighted in FIG. 2. Based upon assignments from the literature and our laboratory, absorption bands in these regions can be attributed to oxy- and deoxyhaemoglobin, oxidised and reduced cytochrome $aa_3$ and tissue lipids and proteins, as shown in FIG. 2. Specifically, oxyhaemoglobin and deoxyhaemoglobin indicate oxygen delivery to the synovium and surrounding tissue while the redox balance cytochrome aa3 provides a measure of mitochondrial oxygen utilisation. Interestingly, changes in these spectra regions have been observed in studies of ischaemic tissues in our laboratory, suggesting that multivariate analysis of NIR spectra of joints affected by RA detects changes in the joints associated with ischaemia.

EXAMPLE V

Conclusions

Clearly this novel spectroscopic technique has the potential for non-invasive assessment of joint chemistry. NIR spectroscopy is able to measure the wavelengths of near infrared light that are absorbed by a sample to produce a characteristic chemical fingerprint of the sample. NIR light is absorbed to promote vibrations within molecules. The wavelength of light which are absorbed depend on the nature of the vibration (stretching, bending etc) and the nature of the molecules in the bond. In addition, NIR light can be absorbed to promote low-lying electronic transitions in the metal ions found in proteins such as haemoglobin, myoglobin and cytochromes. The wavelength of light absorbed by the metal ions is influenced by both the oxidative state and local environment. Thus, oxy- and deoxyhaemoglobin and reduced and oxidised cytochrome $aa_3$ each give rise to a characteristic near infrared spectrum. Analysis of the wavelengths of near infrared light absorbed by tissues therefore provides direct compositional (chemical) and physiological (oxygenation and oxygen utilisation) information. Furthermore, near infrared spectroscopy is sensitive to changes in these parameters, providing a method to monitor changes tissue chemistry and physiology associated with disease processes. More importantly, measurements can be made non-invasively by directing the near infrared light onto a sample, in this case a joint, through a fibre optic cable. Light reflected from the joint is then collected and transmitted to the near infrared sensor and the wavelengths of light absorbed by the joint calculated to produce a spectrum.

Near infrared spectra were acquired from MCP and PIP joints. The MCP and PIP joints were studied for two important reasons. Firstly, these joints are quite superficial allowing adequate penetration of the infrared beam into the joint. Near infrared light is scattered by tissues: the greater the thickness of tissue to be traversed by the infrared light, the more the light is scattered. Thus for thick layers of tissue a large proportion of the near infrared light is diffusely scattered and most of this diffusely scattered light cannot be collected by the fibre optic collection. Thus, the hand joints are ideally suited for this technique, having minimal skin and subcutaneous fat overlying them. Secondly, MCPs and PIPs are the most characteristically involved joints in rheumatoid arthritis and are often involved at a very early stage. Correlation with radiographic data can be readily achieved in these joints, which demonstrate the characteristic erosive changes of RA earlier than other joints.

The combination of near infrared spectroscopy and multivariate pattern recognition techniques can be used to distinguish between control joints and those affected by rheumatoid arthritis with a high degree of accuracy. Furthermore, it is possible to classify joints affected by rheumatoid arthritis as being at either an early or a late stage of the disease with a similar degree of accuracy.

Thus, the multivariate analysis method is trained using a large data set acquired from joints of a number of patients. It then determines the patterns in the data set that correlate with early RA, late RA or control joints. A spectrum of a new joint is then analyzed to see which of these patterns is present.

In other embodiments, other inflammatory and/or ischemic conditions of the joint are diagnosed using the above-described device. In these embodiments, the database contains spectra from the condition of interest and the patient spectrum is compared to these.

While the preferred embodiments of the invention have been described above, it will be recognized and understood that various modifications may be made therein, and the appended claims are intended to cover all such modifications which may fall within the spirit and scope of the invention.

TABLE 1

Patient demographics

|  | Early RA | Late RA |
|---|---|---|
| Age | 56 (±8) | 52 (±11) |
| Disease duration (yrs) | 1.2 (±0.7) | 10.9 (±6.2)* |
| Sex - Female (%) | 21 (75%) | 18 (72%) |
| Ethnicity |  |  |
| Caucasian | 20 (71.4%) | 23 (92%) |
| Native American | 6 (21.4%) | 2 (8%) |
| Asian | 1 (3.6%) |  |
| Black | 1 (3.6%) |  |
| Skin colour (1–4) | 2.2 (±1.0) | 1.6 (±0.6) |
| Smoker (%) | 7 (25%) | 4 (±16%) |
| AM stiffness (min) | 110 (±160) | 116 (±60) |
| Pain scale (0–10) | 3.9 (±2.7) | 3.7 (±3.0) |
| HAQ | 0.57 (±0.37) | 0.52 (±0.5) |
| DMARD (%) | 20 (71.4%) | 15 (60%) |
| Steroid (%) | 8 (28%) | 6 (24%) |
| NSAID (%) | 19 (67.9%) | 19 (76%) |

*Difference significant, $p < 0.05$.

TABLE 2

Grip strength, total joint counts and laboratory parameters.

|  | Early RA (n = 28) | Late RA (n = 25) |
|---|---|---|
| Total joint count |  |  |
| Tender | 15.0 (±11.4) | 14.4 (±11.1) |
| Swelling | 10.9 (±9.9) | 15.2 (±10.1)* |
| Damaged | 1.0 (±1.6) | 9.6 (±10.8)** |
| ESR | 30.5 (±14.7) | 17.3 (±6.2) |
| CRP | 14.7 (±9.0) | 25.2 (±23) |

*Difference significant, $p = 0.035$.
**Difference significant, $p = 0.00044$

TABLE 3

Two Class LDA: Early RA and Late RA, PIP Only

|  | Control | Early RA | Sensitivity (% correct) | of | Specificity | Positive Predictive Value | Negative Predictive Value |
|---|---|---|---|---|---|---|---|
| Early RA | 26 | 11 | 70.3 | 37 | 52.9 | 59.9 | 64.0 |
| Late RA | 16 | 18 | 52.9 | 34 | 70.3 | 64.0 | 59.9 |
| Totals | 42 | 29 |  | 71 |  |  |  |

Overall Accuracy: 61.6%

TABLE 4

Two Class LDA: Early RA and Late RA, MCP Only

|  | Con- trol | Early RA | Sensitivity (% correct) | of | Speci- ficity | Positive Predictive Value | Negative Predictive Value |
|---|---|---|---|---|---|---|---|
| Early RA | 30 | 8 | 78.8 | 38 | 72.7 | 74.3 | 77.6 |
| Late RA | 9 | 24 | 72.7 | 33 | 78.9 | 77.6 | 74.3 |
| Totals | 39 | 32 |  | 71 |  |  |  |

Overall Accuracy: 75.8%

TABLE 5

Two Class LDA: Early RA and Late RA, Both MCP and PIP

|  | Early RA | Late RA | Sensitivity (% correct) | of | Spe- cifi- city | Positive Predictive Value | Negative Predictive Value |
|---|---|---|---|---|---|---|---|
| Early RA | 58 | 17 | 77.3 | 75 | 71.2 | 72.9 | 75.9 |
| Late RA | 19 | 47 | 71.2 | 66 | 77.3 | 75.9 | 72.9 |
| Totals | 77 | 64 |  | 141 |  |  |  |

Overall Accuracy: 74.3%

TABLE 6

Three Class LDA: Control, Early RA and Late RA (all joints)

|  | Control | Early RA | Late RA | Sensitivity (% correct) | of | Specificity | Positive Predictive Value | Negative Predictive Value |
|---|---|---|---|---|---|---|---|---|
| Control | 73 | 13 | 8 | 77.7% | 94 | 91.7% | 82.4% | 89.1% |
| Early RA | 17 | 153 | 35 | 74.6% | 205 | 82.2% | 67.7% | 86.6% |
| Late RA | 16 | 42 | 135 | 69.9% | 193 | 87.2% | 73.2% | 85.3% |
| Totals | 106 | 208 | 178 |  | 492 |  |  |  |

Overall Accuracy: 74.1%

What is claimed is:

1. A non-invasive method of diagnosing an inflammatory or ischaemic condition in a joint comprising:
   providing a device having:
      an emitter arranged to non-invasively emit a beam of infrared light into a joint;
      a collector arranged to collect and analyze reflected light, said collector for producing an infrared spectrum; and
      a database containing a plurality of spectra previously collected from joints, said spectra being divided into at least two groups an afflicted group comprising spectra from joints diagnosed as having the inflammatory or ischaemic condition and a control group comprising spectra from nonafflicted joints;
   providing a joint;
   positioning the device proximal to the joint such that the emitter contacts tissue surrounding the joint non-invasively;
   emitting a beam of near infrared light from the emitter into the joint;
   collecting and analyzing reflected light from the joint, thereby producing a patient spectrum;
   comparing the patient spectrum to the plurality of spectra in the database; and
   assigning the patient spectra to either the afflicted group or the control group based on said comparison, thereby non-invasively diagnosing the joint as having or not having the inflammatory or ischaemic condition.

2. The method according to claim 1 wherein the inflammatory or ischaemic condition is rheumatoid arthritis.

3. The method according to claim 2 wherein the database spectra are divided into three groups: control, early rheumatoid arthritis and late rheumatoid arthritis.

4. The method according to claim 1 wherein the patient spectrum is a mean spectrum of two or more spectra of the joint.

5. The method according to claim 1 wherein the patient spectrum is compared to the database spectra over wavelengths of high accuracy.

6. The method according to claim 5 wherein the wavelengths of high accuracy are selected from the group consisting of: wavelengths corresponding to oxyhemoglobin to deoxyhemoglobin ratio; wavelengths corresponding to reduced cytochrome $aa_3$; wavelengths corresponding to oxidized cytochrome $aa_3$; wavelengths corresponding to deoxyhemoglobin; wavelengths corresponding to oxyhemoglobin; wavelengths corresponding to cytochrome $aa_3$; wavelengths corresponding to water, wavelengths corresponding to proteins; wavelengths corresponding to lipids; and combinations thereof.

7. The method according to claim 1 wherein the emitter is a fibre optic probe.

8. A device for non-invasively diagnosing an inflammatory or ischaemic condition in a joint comprising:
   an emitter arranged to emit a beam of infrared light into a joint non-invasively;
   a collector for producing an infrared spectrum from reflected infrared light; and
   an analyzer including a database containing a plurality of prior spectra previously collected from joints, said spectra being divided into at least two groups: an afflicted group comprising spectra from joints diagnosed as having the inflammatory or ischaemic condition and a control group comprising spectra from nonafflicted joints, said analyzer including an algorithm arranged to compare said produced spectrum to said prior spectra in the database at wavelengths of high accuracy, said wavelengths selected from the group consisting of: wavelengths corresponding to a ratio of oxyhemoglobin to deoxyhemoglobin; wavelengths corresponding to reduced cytochrome $aa_3$; wavelengths corresponding to oxidized cytochrome $aa_3$; wavelengths corresponding to deoxyhemoglobin; wavelengths corresponding to oxyhemoglobin; wavelengths corresponding to cytochrome $aa_3$; wavelengths corresponding to water wavelengths corresponding to proteins; wavelengths corresponding to lipids: and combinations thereof and assign said produced spectrum to either the afflicted group or the control group based on said comparison.

9. The device according to claim 8 wherein the collector produces a spectrum that is a mean spectrum comprised of two or more spectra of the joint.

10. The device according to claim 8 wherein the emitter is a fibre optic probe.

11. A non-invasive method of diagnosing an inflammatory or ischaemic condition in a joint comprising:
   providing a device having;
      an emitter arranged to emit a beam of infrared light;
      a collector arranged to collect and analyze reflected light, said collector for producing an infrared spectrum; and
      a database containing a plurality of spectra previously collected from joints, said spectra being divided into at least two groups: an afflicted group comprising spectra from joints diagnosed as having the inflammatory or ischaemic condition and a control group comprising spectra from nonafflicted joints;
   providing a joint;
   positioning the device proximal to the joint such that the emitter non-invasively contacts tissue surrounding the joint;
   emitting a beam of near infrared light from the emitter into the joint;
   collecting and analyzing reflected light from the joint, thereby producing a patient spectrum;
   comparing the patient spectrum to the plurality of spectra in the database at wavelengths of high accuracy shown in (FIG. 2), said wavelengths selected from the group consisting of: wavelengths corresponding to reduced cytochrome $aa_3$; wavelengths corresponding to oxidized cytochrome $aa_3$; wavelengths corresponding to deoxyhemoglobin; wavelengths corresponding to oxyhemoglobin; wavelengths corresponding to cytochrome $aa_3$; wavelengths corresponding to water: wavelengths corresponding to proteins; wavelengths corresponding to lipids; and combinations thereof; and
   assigning the patient spectra to either the afflicted group or the control group based on said comparison, thereby non-invasively diagnosing the joint as having or not having the inflammatory or ischaemic condition.

12. The method according to claim 11 wherein the inflammatory or ischaemic condition is rheumatoid arthritis.

13. The method according to claim 11 wherein the patient spectrum is a mean spectrum of two or more spectra of the joint.

14. The method according to claim 11 wherein the data base spectra are divided into three groups, control, early rheumatoid arthritis and late rheumatoid arthritis.

* * * * *